United States Patent [19]

Moon

[11] Patent Number: 4,986,109

[45] Date of Patent: Jan. 22, 1991

[54] ABRASION-PROOF TESTER

[75] Inventor: Bum K. Moon, Seoul, Rep. of Korea

[73] Assignee: Goldstar Co., Ltd., Seoul, Rep. of Korea

[21] Appl. No.: 440,262

[22] Filed: Nov. 22, 1989

[30] Foreign Application Priority Data

Nov. 25, 1988 [KR] Rep. of Korea .................. 15577

[51] Int. Cl.$^5$ .............................................. G01N 3/56
[52] U.S. Cl. .......................................................... 73/7
[58] Field of Search ...................... 73/7, 865.5, 866; 209/237–239, 680

[56] References Cited

U.S. PATENT DOCUMENTS

| 3,065,627 | 11/1962 | Ross | 73/7 |
| 4,233,151 | 11/1980 | Gundlach | 209/237 |
| 4,381,669 | 4/1983 | Peters | 73/865.5 |

FOREIGN PATENT DOCUMENTS

| 0155555 | 6/1982 | Fed. Rep. of Germany | 73/7 |
| 0991252 | 1/1983 | U.S.S.R. | 73/7 |
| 0993100 | 1/1983 | U.S.S.R. | 73/7 |

OTHER PUBLICATIONS

Tsesnek, "An Apparatus for Studying Friction and Wear Processes of Solid Surfaces", Opt. Mekh, The Optical Society of America, Sov. J. Opt. Technol, Taber Brochere, May 1957.
Allen-Bradley Sonic Sifter, Aug. 1965.
ASTME, D2714–68, Std Method for Calibration and Operation of the Alpha Model LFW-1, Friction and Wear Testing Machine, pp. 205-210, 1968.

Primary Examiner—Robert Raevis
Attorney, Agent, or Firm—Birch, Stewart, Kolasch & Birch

[57] ABSTRACT

An abrasion-proof tester for analyzing granularity of abraded powder includes abrasive material adhered on a abrasive plate fixed on a driving shaft of a variable speed motor is closely contacted with test pieces supported by supporter which is resiliently supported and uniformly pressed by compression spring and multiple stage granularity measuring device oscillated by oscillating plate is mounted at a side of said abrasive plate which is heated by electric heater controlled by digital temperature sensor and chromel-alumel thermocouple.

4 Claims, 1 Drawing Sheet

U.S. Patent  Jan. 22, 1991  4,986,109
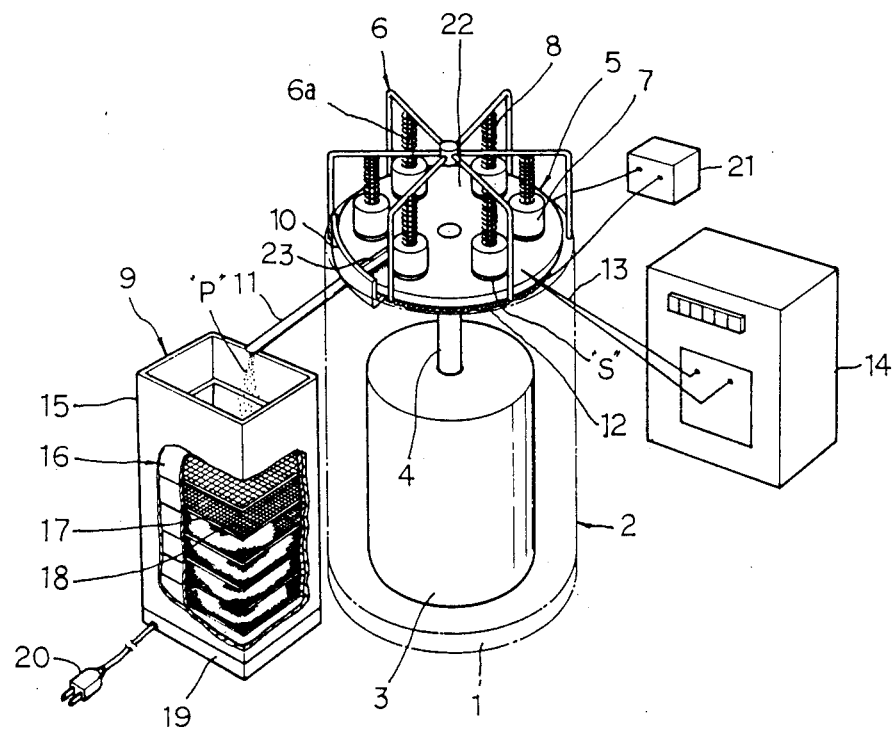

ABRASION-PROOF TESTER

BACKGROUND OF THE INVENTION

The present invention relates to an abrasion-proof tester which is capable of analyzing the granularity of abrasive powder in heating condition, and more particularly to an abrasion-proof tester capable of examining abrasive physical property and fine abrasion-proof test.

In conventional abrasion-proof tester, there has been a reciprocating type abrasion-proof tester in which abrasive material is adhered to a movable plate which moves linearly by the driving force of variable speed driving motor and test piece is adhered to a fixed bar, and the test piece is contacted and being abraded whereby abrasion degree of test piece is measured, and a rotary type abrasion-proof tester has been also known in which abrasive material is adhered to a rotary plate which rotates by the driving force of variable speed driving motor and test piece is adhered to a fixed bar, and said test piece is contacted to the abrasive material and being abraded whereby abrasion degree of test piece is measured.

Typical kinds of said abrasive materials are sand paper, grind stone and the like, and the applying abrasive material is varied depending upon the material to be tested. That is, sand paper is widely used for measuring the abrasion degree simply, and rubber abrasive material is used for plastic material and thin film, and sand paper and grind stone and the like are jointly used for metal and ceramic materials.

Abrasion degree is calculated with mainly two kinds of method, in which the first is to calculate the change of weight in response to the number of abrasing by collecting the abraded powder produced upon grinding off the test piece, whereby abraded degree is calculated by comparing with several standard abrasion data. The second is to calculate the abrasion degree by calculating the change of the weight of test piece by continuously weighing the test piece after abrading a predetermined number of times.

In conventional abrasion-proof testers as aforementioned, inasmuch as a user has to directly collect the abraded powder during abrasion test with brush, and straining with sieve and separating by granularity, and then analyzing the granularity by SEM (scanning electron microscope), processing period of time becomes extended and yield of abrasion test is reduced. And since all materials have very close relation with applying temperature of material, abrasion-proof value of the material can be appropriate data capable of defining the abrasive physical property of material upon actual using only when the relation in response to the temperature being necessarily exhibited. However since the temperature of material in conventional abrasion-proof tester is fixed to only normal temperature in the temperature of abrasive material, presumption of abrasive property of material is practically difficult.

SUMMARY OF THE INVENTION

The object of the present invention is to provide an abrasion-proof tester capable of analyzing the granularity of abrasive powder in heating condition which can eliminate the disadvantages encountered in the conventional testers.

In the abrasion-proof tester of the present invention, an abrasive plate fixed to a driving shaft of variable speed motor and turning therewith is formed with stainless steel plate of good in heat conductivity and corrosion-proof property, at the same time, attaching nichrome wire to said abrasive plate and executing the abrasion test with heating at appropriate temperature whereby enabling the examination of abrasive property at a predetermined temperature condition, and multiple stage granularity measuring apparatus oscillated by oscillating plate is provided at a side of abrasive plate so that abraded powder of the test piece abraded out of the abrasive plate is automatically separated by granularity and enabling to observe.

BRIEF DESCRIPTION OF THE DRAWINGS

The accompanying single drawing is a perspective view of abrasion-proof tester according to the present invention which is partly cut out.

DETAILED DESCRIPTION OF THE INVENTION

Hereinafter, the present invention will be described in detail with reference to the accompanying drawings.

The abrasion-proof tester of the present invention is constituted in such that a variable speed motor 3 is mounted within a cylinder 2 on a table 1, an abrasive plate 5 is rotatably fixed to a driving shaft 4 of a motor 3, vertical supporting rods 6a are formed integrally with each radial supporting rod 6 fixed to the top of cylinder 2, respectively, and test piece supporting means 7 for closely contacting, test pieces "S" to said abrasive plate 5 are fixed to each vertical supporting rod 6a so as to urge downwardly by compression coil springs 8, a granularity measuring device 9 is provided at a side of said cylinder 2, an abraded powder collecting curve corner 10 is mounted at a side of periphery of abrasive plate 5, at the same time, a slant discharging tube 11 is connected to said abraded powder collecting curve corner 10 whereby the abraded powder "P" of test pieces is made to discharge through the slant discharging tube 11 into the granularity measuring device 9 since one end of the tube 11 communicates with the collecting curve corner 10 and the abraded powder P is forced by the rotational force of the abrasive plate 5, and a heater for heating the abrasive plate 5 is mounted on the top of the cylinder 2 through intermediary of isolation material.

As a material for the abrasive plate 5, stainless steel (304 SUS) or the like can be utilized which has a good heat conductivity and corrosion-resistant property and its thickness is about 1 cm. Said abrasive plate 5 is very much precisely finished so that error in roughness is made to be included within the range of ±0.1 mm. The reason for using said abrasive plate 5 with a strong material against corrosion is because chemical solvent such as methanol or acetone is mainly used for removing a hot adhesive material after finishing the abrasion test inasmuch as the hot adhesive material is on the abrasive plate 5 for adhering the abrasive material so as to attach the test piece supporting means 7 to the abrasive plate 5. The temperature of said abrasive plate 5 is made to be able to measure by utilizing C—A (Chromel—Alumel) thermocouple 13 and being made to be able to digitalize by means of an A/D converter for obtaining a proper temperature required to test the features of the abraised powder depending on the temperature range. Reference numeral 14 represents a digital temperature sensor in which the A/D converter is contained.

For heating the abrasive plate 5, it is possible to use an electric heater in which heat isolation plate is mounted on the top surface of cylinder 2, and nichrome wire 12 is mounted on said heat isolation plate in spiral shape.

The granurality measuring device 9 is constructed such that a mesh unit 16 is mounted within the interior of housing 15 of rectangular or circular in cross section made of transparent synthetic resin as well as an oscillating plate 19 is provided at the bottom end thereof. The mesh unit 16 includes eight sieves 17 that mesh number is gradually increasing from the top to the bottom, and mesh sizes of net 18 of each sieve 17 are made from the top as 50, 20, 10, 5, 1, 0.1, 0.1 less than 0.05 (unit is $\mu$m).

Each sieve 17 of said mesh unit 16 may have rectangular or circular cross section so as to be loaded easily within the housing 15, and frames of the sieves are formed with transparent synthetic resin such that condition of sieving the abraded powder can be observed outside.

Generally, large particle of abraded powder is more than 50$\mu$m, which is sieved by the top stage sieve of mesh unit 16, and being decreased gradually during passing through the mesh unit 16 sequentially, and finally very fine powder less than 0.05$\mu$m is sieved by the bottom stage sieve, whereby very small particle of abrasion value can be intuitionally discriminated.

The abrasion rate of abrasion test piece is to be observed by relative quantity of powder sieved through the mesh unit 16 of eight stages 17, and when the quantity of the powder at the small-sized sieve 17 is large, it means that the abrasion test piece is an abrasion-proof material.

In the drawing, reference numeral 20 shows a plug for applying power source to oscillation plate 17, numeral 21 shows variable voltage supply means for applying power source to the motor 3 and nichrome wire 12, numeral 22 is abrasive material adhered to the top surface of abrasive plate 5, and numeral 23 shows a brush fixed to the wall of abraded powder collecting means 10.

In case of executing the abrasion test by utilizing the abrasive tester of the present invention constructed as aforementioned, firstly adhesive material is applied on the abrasive plate 5 and abrasive material 22 such as sand paper is adhered thereto and then test pieces S are respectively attached to the bottom surfaces of test piece supporting means 7, at this moment, each test piece S should be contacted on the abrasive material 22 with uniform pressure. And thereafter, power is applied to the nichrome wire 12 for heating by the voltage supply means 21 and being heated, and the temperature is identified by the digital temperature sensor 14 connected with thermocouple 13, and when it has become a predetermined temperature, power is supplied to the motor 3 by the voltage supply means 21 and rotating with appropriate speed for a predetermined period of time. Thus, when the abrasive plate 5 is rotated, the test pieces S are abraded by the abrasive material 22, and abraded powder P is collected by the abraded powder collecting brush 23, and then being flowed gradually into the granularity measuring device 9 through the discharging tube 11.

Thus, in response to the abrasion being proceeded, the abraded powder is made to pass well through the mesh unit 16 consisted of eight sieves 17 by oscillating the oscillating plate 19 whereby the abraded powder is made to be separated by each granularity, and abrading operation is stopped. Although the abraded powder remaining on the abrasive plate 5 is substantially almost negligible quantity, it is preferable to sweep the remaining power into the granularity measuring device 9 with separate collecting brush.

Thus when the abrasive operation is finished, each sieve 17 of mesh unit 16 is taken out of the housing 15, and the weight of abraded powder is measured per granularities, or for the purpose of examining the form and property of abrasive powder, it is observed by metal microscope and electronic microscope.

The abrasion tester of the present invention as aforementioned can test the condition of abrasive property and examines the condition of general abrasive powder, so that efficiency of abrasion-proof test of material can be enhanced.

Since above-described present invention is possible to examine the abrasive property in a desired temperature condition, reliable value about applicable possibility and reliability related to the data of abrasive rate of material is enhanced.

Further, grasping of intuitional abrasive condition is possible by the observation of granularity of abrasive powder, and according to the observation of abraded powder separated by sizes, not only the grasping of abrasion mechanism in response to the materials is very easy but also cost is cheaper and manufacturing process becomes simple.

What is claimed is:

1. An abrasion-proof tester capable of analyzing the granularity of abraded powder, which comprises:
    a table;
    a cylinder disposed on said table;
    a variable speed motor mounted within said cylinder;
    an abrasive plate fixed to a driving shaft of said variable speed motor;
    a plurality of supporting bars fixed to the top of said cylinder and provided with perpendicular supporting bars at the middle thereof;
    test piece supporting means for closely contacting test pieces to said abrasive plate and being elastically supported to said perpendicular supporting bars by compression of a coil spring, respectively;
    a granularity measuring device disposed at a side of said cylinder for measuring the granularity of abraded powder and separating the abraded powder, said granularity measuring device including several sieves disposed within a housing thereof and a number of meshes which are sequentially increased from the top sieve to the bottom sieve;
    abraded powder collecting curve corner disposed at a side of periphery of said abrasive plate;
    a discharging tube communicated with said abraded powder collecting curve corner for discharging the abraded powder of test pieces into said granularity measuring device; and
    a heater for heating said abrasive plate is mounted on the top surface of said cylinder.

2. An abrasion-proof tester according to claim 1, wherein said heater is an electric heater including a nichrome wire fixed to the top surface of said cylinder through the intermediary of isolation material.

3. An abrasion-proof tester according to claim 1, wherein said abrasive plate is formed of material which is not corroded when removing the abrasive material adhered thereon with chemical agent such as methanol or acetone.

4. An abrasion-proof tester according to claim 1, further including;
    a thermocouple for measuring the temperature of said abrasive plate, and a temperature sensor including an A/D converter for displaying the measured temperature as a digital number.

* * * * *